(12) United States Patent
Fischer et al.

(10) Patent No.: US 7,220,895 B2
(45) Date of Patent: May 22, 2007

(54) METHODS AND COMPOSITIONS FOR DIRECTING EXPRESSION OF A HETEROLOGOUS NUCLEIC ACID IN PLANTS

(75) Inventors: Robert L. Fischer, El Cerrito, CA (US); Yukiko Mizukami, Kensington, CA (US)

(73) Assignee: Regents of the University of California, Oakland, CA (US)

( * ) Notice: Subject to any disclaimer, the term of this patent is extended or adjusted under 35 U.S.C. 154(b) by 335 days.

(21) Appl. No.: 10/623,477

(22) Filed: Jul. 18, 2003

(65) Prior Publication Data

US 2005/0132445 A1    Jun. 16, 2005

Related U.S. Application Data

(63) Continuation of application No. 09/479,855, filed on Jan. 8, 2000, now Pat. No. 6,639,128, which is a continuation-in-part of application No. 09/227,421, filed on Jan. 8, 1999, now Pat. No. 6,559,357.

(51) Int. Cl.
*C12N 15/82* (2006.01)
(52) U.S. Cl. ..................... 800/287; 536/24.1
(58) Field of Classification Search ............... 536/24.1; 800/287
See application file for complete search history.

(56) References Cited

U.S. PATENT DOCUMENTS

| 5,110,732 A | 5/1992 | Benfey et al. |
| 6,559,357 B1 | 5/2003 | Fischer et al. |
| 6,639,128 B1 | 10/2003 | Fischer et al. |

FOREIGN PATENT DOCUMENTS

WO    WO 00/40694 A2    7/2000

OTHER PUBLICATIONS

Kim Y et al. A 20 nucleotide upstream element is essential for the nopaline synthase (nos) promoter activity. Plant Mol Biol. Jan. 1994;24(1):105-17.*
Kosugi S. et al. Two of three promoter elements identified in a rice gene for proliferating cell nuclear antigen are essential for meristematic tissue-specifc expression. Plant J. Jun. 1995;7(6):877-86.*
Klucher, K.; Database PIR, Accession No. S71365, Gene Sequence, Oct. 28, 1996.

Klucher et al.; "The AINTEGUMENTA gene of Arabidopsis required for ovule and female gametophyte development is related to the floral homeotic gene APETALA2"; 1996, *The Plant Cell*, vol. 8, pp. 137-153.
Krizek, Beth A.; "Ectopic Expression of *AINTEGUMENTA* in *Arabidopsis* Plants Results in Increased Growth of Floral Organs"; *Developmental Genetics* 1999, vol. 25, pp. 224-236.
Krizek, Beth A.; "AINTEGUMENTA utilizes a mode of DNA recognition distinct from that used by proteins containing a single AP2 domain"; 2003, *Nucleic Acids Research*, vol. 31, No. 7, pp. 1859-1868.
Elliott et al.; "AINTEGUMENTA , an APETALA2-like gene of Arabidopsis with pleiotropic roles in ovule development and floral organ growth"; 1996, *The Plant Cell*, vol. 8, pp. 155-168.
Mizukami, Yukiko et al.; "Plant organ size control: *AINTEGUMENTA* regulates growth and cell numbers during organogenesis"; *PNAS* 2000, vol. 97 No. 2 pp. 942-947.
Nole-Wilson S., et al.; "DNA binding properties of the Arabidopsis floral development protein AINTEGUMENTA"; 2000, *Nucleic Acids Research*, vol. 28, No. 21, pp. 4076-4082.
SPTREMBL Accession No. Q42462, Nov. 1, 1996, ovule development protein AINTEGUMENTA from *Arabidopsis thaliana*.
Doerks et al, "Protein annotation: detective work for function prediction", Jun. 1998 TIG vol. 14 No. 6, pp. 248-250.
Elliott et al, GenBank Accession No. U41339, Oct. 23, 1996.
Elliot et al. , SPTREMBL Accession No. Q42462, Ovule Development Protein Aintegumenta from *Arabidopsis thaliana*, Nov. 1, 1996.
Klucher et al, GenBank Accession No. U40256, Feb. 29, 1996.
Lim et al, GenBank Accession No. L46470, Dec. 21, 1995.
Long, et al., "The development of apical embryonic pattern in Arabidopsis"; Development 125, pp. 3027-3035 (1998).
Matsuoka et al., Plant Cell 5: 1039-1048, Sep. 1993.
Mizukami, Y. et al.; "Functional domains of the floral regulator AGAMOUS: Characterization of the DNA binding domain and analysis of dominant negative mutations"; 1996, Plant Cell, vol. 8, No. 5, pp. 831-845.
Putterill et al. Mol. Gen. Genet. 239: 145-157, 1993.
Putterill et al. Cell 80: 847-857, Mar. 1995.
Schneitz, et al., "Pattern formation and growth during floral organogenesis: HUELLENLOS and AINTEGUMENTA are required for the formation of the proximal region of the ovule primordium in *Arabidopsis thaliana*"; Development 125, pp. 2555-2563 (1998).
Smith et al. Nature. 1988. vol. 334:724-726.
Vergani et al Genbank Accession No. U44028, Jan. 30, 1996.
Vergani et al., SPTREMBL Accession No. Q38914, from *Arabidopsis thaliana*, Nov. 1, 1996.

* cited by examiner

*Primary Examiner*—Cynthia Collins
(74) *Attorney, Agent, or Firm*—Townsend and Townsend and Crew LLP

(57) ABSTRACT

The invention provides for a methods and compositions for directing expression of a heterologous nucleic acid in plants.

3 Claims, No Drawings

METHODS AND COMPOSITIONS FOR DIRECTING EXPRESSION OF A HETEROLOGOUS NUCLEIC ACID IN PLANTS

CROSS REFERENCE TO RELATED APPLICATIONS

This application is a continuation of U.S. patent application Ser. No. 09/479,855, filed Jan. 7, 2000, now U.S. Pat. No. 6,639,128, issued Oct. 28, 2003, which is a continuation-in-part of U.S. patent application Ser. No. 09/227,421, filed Jan. 8, 1999, now U.S. Pat. Ser. No. 6,559,357, issued May 6, 2003, each of which is incorporated by reference.

FIELD OF THE INVENTION

The present invention is directed to plant genetic engineering. In particular, it relates to methods of altering organ mass, controlling fertility and enhancing asexual reproduction in plants through the modulation of plant growth and cell proliferation.

BACKGROUND OF THE INVENTION

Control of organ mass/size and fertility in plants is a significant goal in commercial agriculture. Plant shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (the mature ovary) and seedlings are the harvested product of numerous agronomically-important crop plants. Therefore the ability to manipulate the size/mass of these organs/structures through genetic control would be an important agricultural tool. Similarly, induction of sterility in plants is useful in limiting plant pollination and reproduction until it is economically desirable. For example, male sterile plants are often desirable in crops where hybrid vigor increases yield.

The intrinsic plant organ size is determined genetically, although it can be altered greatly by environment signals (e.g. growth conditions). In general, larger organs consist of larger numbers of cells. Since neither cell migration nor cell death plays a major role during plant development, the number of cells in plant organs depends on cell proliferation. Precise regulation of cell proliferation is also necessary for proper development of reproductive organs that make plants fertile. While some basic research has identified genes involved in plant organ development and fertility, little is known about genetic control of cell proliferation or its link to organogenesis including organ size/mass control and fertility in plants. Therefore an important goal is to understand the connection between genes that control organogenesis and genes that control cell proliferation. A great deal of basic research has shown that the components (e.g., cyclin dependent kinases, cyclins and their inhibitors) and mechanisms (e.g., regulation by phosphorylations, ubiquitin-mediated proteolysis) that control the cell cycle in yeast and animals are conserved in higher plants (Burssens, et al. *Plant Physiol Biochem.* 36:9–19 (1998)).

In *Arabidopsis*, the developing flower includes the ovule. Wild-type ovule development in *Arabidopsis* has been extensively analyzed (Robinson-Beers et al., *Plant Cell* 4:1237–1249 (1992); Modrusan, et al. *Plant Cell.* 6:333–349 (1994) and Schneitz et al., *Plant J.* 7:731–749 (1995)). A variety of mutations that affect ovule development have been identified (Klucher et al., *Plant Cell* 8:137–153 (1996); Elliott et al., *Plant Cell.* 8:155–168 (1996); Baker, et al. *Genetics.* 145:1109–1124 (1997); Robinson-Beers, et al., *Plant Cell.* 4:1237–1249 (1992); Modrusan et al. *Plant Cell.* 6:333–349 (1994); Ray, A., et al. *Proc Natl Acad Sci USA.* 91:5761–5765 (1994); Lang, et al., *Genetics* 137:1101–1110 (1994); Leon-Kloosterziel Plant Cell. 6:385–392 (1994); Gaiser et al., *Plant Cell* 7:333–345 (1995)), and some of them have been found that specifically affect patterns of cell division (Schneitz, et al. *Development.* 124:1367–1376 (1997)). Of those, several genes have been cloned; *AINTEGUMENTA* (*ANT*) (Klucher et al. *Plant Cell.* 8:137–153 (1996); Elliott et al., *Plant Cell.* 8:155–168 (1996)), *AGAMOUS*, (Yanofsky et al., *Nature.* 346:35–39 (1990); Bowman et al., *Plant Cell.* 3:749–758 (1991)), *SUPERMAN* (Sakai et al., *Nature.* 378:199–203 (1995)). Because these genes are expressed and function not only in developing ovules but also in various developing organs, analysis of these mutations and genes has provided general information about the control of cell proliferation during plant development.

Another trait important to the manipulation of crop species is the ability to reproduce or propagate plants through asexual means, particularly vegetative propagation of sterile or hybrid plants, and regeneration of plants from transformed cells. Asexual reproduction includes regeneration of plants from cells or tissue, propagation of plants through cutting by inducing adventitious shoots and roots, and apomixis by forming somatic embryos. Asexual reproduction has the advantage that genetic clones of plants with desirable traits can be readily produced. Not all plants, however, can produce adventitious shoots or roots, or regenerate whole plants from cells or tissue.

In spite of the recent progress in defining the genetic control of plant cell proliferation, little progress has been reported in the identification and analysis of genes effecting agronomically important traits such as organ mass/size, fertility, asexual reproduction, and the like through regulating cell proliferation. Characterization of such genes would allow for the genetic engineering of plants with a variety of desirable traits. The present invention addresses these and other needs.

SUMMARY OF THE INVENTION

The present invention provides methods for modulating cell proliferation and thus cell number in plants by modulating ANT activity in plants. Typically, the methods comprise modulating the expression of ANT in plants and selecting for plants with altered size/mass, fertility, or both. In some preferred embodiments, the ANT activity is increased and plants with increased cell proliferation and thus increased cell number are selected. One method for modulating ANT expression is by introducing into a plant an expression cassette containing a heterologous ANT nucleic acid operably linked to a promoter. Examples of possible ANT nucleic acids that can be used include nucleic acids at least 50% identical to SEQ ID NO:1 and SEQ ID NO:4. Other examples include nucleic acids that encode the polypeptides at least 60% identical to either SEQ ID NO:2 or SEQ ID NO:5.

The present invention also provides methods for modulating cell proliferation and thus the production of adventitious organs in plants. Typically, the methods comprise increasing the activity or expression of ANT in plants and selecting for plants with adventitious shoots, organs or structures such as embryos. One method for modulating ANT expression is by introducing into a plant an expression cassette containing a heterologous ANT nucleic acid operably linked to a promoter. Examples of possible ANT nucleic acids that can be used include nucleic acids at least 50% identical to SEQ ID NO:1 and SEQ ID NO:4. Other examples include nucleic acids that encode the polypeptides at least 60% identical to either SEQ ID NO:2 or SEQ ID NO:5.

The present invention also provides methods of reproducing a plant through asexual means. Typically, the methods comprise increasing the activity or expression of ANT in plants and selecting a plant reproduced from the plant cell or tissue. One method for modulating ANT expression is by introducing into a plant an expression cassette containing a heterologous ANT nucleic acid operably linked to a promoter. Examples of possible ANT nucleic acids that can be used include nucleic acids at least 50% identical to SEQ ID NO:1 and SEQ ID NO:4. Other examples include nucleic acids that encode the polypeptides at least 60% identical to either SEQ ID NO:2 or SEQ ID NO:5. In various embodiments, the plant arises from an adventitious shoot, a somatic embryo, or a cutting.

In another embodiment of the invention, a heterologous gene is expressed in meristematic tissue of a plant by introducing into a plant an expression cassette containing an ANT promoter operably linked to a heterologous polynucleotide. In a preferred embodiment of this invention, the ANT promoter is shown in SEQ ID NO:3.

The invention also provides isolated nucleic acid molecules comprising an ANT nucleic acid that specifically hybridizes to SEQ ID NO:4, which is isolated from *Brassica napus*.

A variety of plant promoters can be used in the methods of the invention. The promoter can be constitutive, inducible or specific for an organ, tissue, or cell. In some embodiments a promoter from an ANT gene, e.g. SEQ ID NO:3, is used. Expression of the ANT nucleic acids of the invention can be directed to any desired organ, tissue, or cell in the plant. In some preferred embodiments of the invention, the promoter directs expression of the ANT nucleic acid in shoot vegetative organs/structures, such as leaf, stem and tuber. In other preferred embodiments, the promoter directs expression of the ANT nucleic acid in roots. In other preferred embodiments, the promoter directs expression of the ANT nucleic acid in flowers or floral organs/structures, such as bracts, sepals, petals, stamens, carpels, anthers and ovules. In different embodiments, the promoter directs expression of the ANT nucleic acid in seeds (e.g. embryo, endosperm, and seed coat) or fruit.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells.

The term "plant" includes whole plants, shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (e.g., the mature ovary), seedlings, plant tissue (e.g. vascular tissue, ground tissue, and the like), cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Increased or enhanced ANT activity or expression of the ANT gene" refers to an augmented change in ANT activity. Examples of such increased activity or expression include the following. ANT activity or expression of the ANT gene is increased above the level of that in wild-type, non-transgenic control plants (i.e. the quantity of ANT activity or expression of the ANT gene is increased). ANT activity or expression of the ANT gene is in an organ, tissue or cell where it is not normally detected in wild-type, non-transgenic control plants (i.e. spatial distribution of ANT activity or expression of the ANT gene is increased). ANT activity or expression is increased when ANT activity or expression of the ANT gene is present in an organ, tissue or cell for a longer period than in a wild-type, non-transgenic controls (i.e. duration of ANT activity or expression of the ANT gene is increased).

As used herein, the term "asexual reproduction" refers to the formation of shoots, roots or a whole plant from a plant cell without fertilization. If the formation of the whole plant proceeds through a somatic embryo, the asexual reproduction can be referred to as apomixis.

The term "adventitious organ" and "adventitious shoot" refer to an organ (e.g. stem, leaf, or root) and a shoot arising in a place other than its usual site, respectively. For example, a root developing on a stem, or a shoot bud arising on a stem in a place other than the axil of a leaf. Adventitious organs or shoots may also arise in callus tissue in vitro. Such adventitious organs or shoots can then used to regenerate a whole plant using methods well known to those of skill in the art.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as a $T_1$ (e.g. in *Arabidopsis* by vacuum infiltration) or $R_0$ (for plants regenerated from transformed cells in vitro) generation transgenic plant. Transgenic plants that arise from sexual cross or by selfing are descendants of such a plant.

An "ANT nucleic acid" or "ANT polynucleotide sequence" of the invention is a subsequence or full length polynucleotide sequence (SEQ ID NO:1) which, encodes a polypeptide (SEQ ID NO:2) and its complement, as described, for instance, by Klucher et al., *Plant Cell* 8:137–153 (1996) and Elliott et al., *Plant Cell.* 8:155–168 (1996) (see, also, GenBank Accession Nos. U40256 and U41339). SEQ ID NO:4, which encodes SEQ ID NO:5, represents another "ANT nucleic acid" from *Brassica*. ANT gene products of the invention are characterized by the presence of an AP2 domain, first identified in AP2, this motif is characterized by a region of approximately 60–70 amino acid residues with a highly conserved core region with the capacity to form an amphipathic α-helix and/or to bind DNA (Jofuku et al., *Plant Cell* 6:1211–1225 (1994); Ohme-Takagi and Shinshi, *Plant Cell* 7:173–182 (1995). The full length ANT protein contains two AP2 domains (amino acids 281 to 357 and from 383 to 451 of SEQ ID NO:2) and a linker region (amino acids 358 to 382), and the homology to other AP2 domain proteins is restricted to this region. An ANT polynucleotide of the invention typically comprises a coding sequence at least about 30–40 nucleotides to about 2500 nucleotides in length, usually less than about 3000 nucleotides in length. Usually the ANT nucleic acids of the invention are from about 100 to about 5000 nucleotides, often from about 500 to about 3000 nucleotides in length.

In the case of both expression of transgenes and inhibition of endogenous genes (e.g., by antisense, or co-suppression) one of skill will recognize that the inserted polynucleotide sequence need not be identical, but may be only "substantially identical" to a sequence of the gene from which it was derived. As explained below, these substantially identical variants are specifically covered by the term ANT nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ANT nucleic acid", "ANT polynucleotide" and their equivalents. In addition, the terms specifically include those full length sequences substantially identical (determined as described below) with an ANT polynucleotide sequence and that encode proteins that retain the function of the ANT polypeptide (e.g., resulting from conservative substitutions of amino acids in the ANT polypeptide).

The term "altered fertility" includes any transient or permanent alteration of fecundity including inducing sterility as well as altered initiation of floral development (e.g. flowering time). Sterility can be caused, inter alia, by disruption of pollen development, dehiscence (i.e. male sterility), by disruption of ovule development (i.e. female sterility), or by disruption of pollination/fertilization processes caused by abnormal development of male/female organs (e.g. stigmatic papillae, transmitting tissue of septum). Flowering time is the developmental time or stage when a plant initiates and produces floral tissue.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to a sequence or subsequence that has at least 25% sequence identity with a reference sequence. Alternatively, percent identity can be any integer from 25% to 100%. More preferred embodiments include at least:25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters:default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when:the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising ANT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

DESCRIPTION OF THE PREFERRED EMBODIMENTS

This invention relates to control of cell proliferation and thus cell number in plants by modulating ANT activity in plants. For example, the invention provides molecular strategies for manipulating plant biomass through controlling the number of cells and size/mass of plant shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit (the mature ovary) and seedlings using ANT gene constructs. Thus, by regulating ANT expression transgenic plants with increased or decreased biomass can be produced. In addition, modulating expression of the gene in male or female reproductive organs can lead to sterility through alteration in the pattern of cell proliferation. Thus, male or female sterile transgenic plants can be produced by enhancing or inhibiting ANT gene expression in the appropriate tissues. In yet other embodiments, formation of adventitious organs, shoots, or structures such as somatic embryos can be controlled using this method of the invention. Thus, the efficiency of asexual reproduction of plants, in particular reproduction of sterile or hybrid plants with desired traits and regeneration of transgenic plants from transformed tissue, can be improved.

Because the ANT gene product most likely functions as a transcription factor (Vergani et al., *FEBS Letters*. 400: 243–246 (1997)), one of skill will recognize that desired phenotypes associated with altered ANT activity can be obtained by modulating the expression or activity of ANT-regulated genes. Any of the methods described for increasing or decreasing ANT expression or activity can be used for this purpose.

Increasing ANT Activity or ANT Gene Expression

Any of a number of means well known in the art can be used to increase ANT activity in plants. Enhanced expression is useful, for example, to induce or enhance asexual reproduction, or increase organ size/mass in desired plant organs. Any organ can be targeted, such as Plant shoot vegetative organs and/or structures (e.g. leaves, stems and tubers), roots, flowers and floral organs (e.g. bracts, sepals, petals, stamens, carpels, anthers), ovules (including egg and central cells), seed (including zygote, embryo, endosperm, and seed coat), fruit and seedlings. The beneficial effects of altering ANT activity need not be the direct result of increased cell proliferation. For instance, increased leaf size/mass will lead to an increase in photosynthesis, which will in turn lead to increased yield. Similarly increased mass/size of roots will lead to increased nutrient uptake and increased yield. Increased stem or pedicel thickness can be used to decreases losses due to breakage, e.g. in cereal crops and fruits.

Increased ANT activity or ANT expression can also be used to produce male or female sterile plants. Male or female sterility is important for agriculture and horticulture, particularly in the production of hybrid varieties that have commercially advantageous superior traits. Male or female sterility allows breeders to make hybrid varieties easily by preventing self-pollen contamination in parental plants. Thus, for instance targeting ANT expression in developing anthers will cause male sterility, but not disrupt female organs thus rendering plants female fertile. Prevention of dehiscence is also desirable for commercial cut flowers. For instance, pollination leads to floral senescence, also pollen grains can be allergenic and in some plants (e.g., lilies) can cause stains.

Expression of the ANT gene in transgenic plants can also cause female sterility. Plants constitutively expressing the ANT gene in ovules produce large mature ovules that are sterile, Therefore, introducing female sterility via controlling ANT function can delay senescence of plants and improve vegetative yield and quality of crop and horticulturally important plants. Alternatively, female sterility can result from decreased ANT expression using methods described below for methods of inhibiting ANT activity or gene expression.

Increasing ANT Gene Expression

Isolated sequences prepared as described herein can be used to introduce expression of a particular ANT nucleic acid to increase endogenous gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, the gene sequences need not be full length, so long as the desired functional domain of the protein is expressed. The distinguishing features of ANT polypeptides, including the AP2 domain, nuclear localization signal, and transcription activation domains, are discussed in Elliot et al. or Klucher et al. above.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Modification of Endogenous ANT Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methariesulfonate and N-nitroso-N-ethylurea. Alternatively, ionizing radiation from sources such as, X-rays or gamma rays can be used.

Alternatively, homologous recombination can be used to induce targeted gene modifications by specifically targeting the ANT gene in vivo (see, generally, Grewal and Klar, *Genetics* 146:1221–1238 (1997) and Xu et al., *Genes Dev.* 10:2411–2422 (1996)). Homologous recombination has been demonstrated in plants (Puchta et al., *Experientia* 50:277–284 (1994), Swoboda et al., *EMBO J.* 13:484–489 (1994); Offringa et al., *Proc. Natl. Acad. Sci. USA* 90:7346–7350 (1993); and Kempin et al. *Nature* 389:802–803 (1997)).

In applying homologous recombination technology to the genes of the invention, mutations in selected portions of an ANT gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91:4303–4307 (1994); and Vaulont et al., *Transgenic Res.* 4:247–255 (1995) are conveniently used to increase the efficiency of selecting for altered ANT gene expression in transgenic plants. The mutated gene will interact with the target wild-type gene in such a way that homologous recombination and targeted replacement of the wild-type gene will occur in transgenic plant cells, resulting in suppression of ANT activity.

Alternatively, oligonucleotides composed of a contiguous stretch of RNA and DNA residues in a duplex conformation with double hairpin caps on the ends can be used. The RNA/DNA sequence is designed to align with the sequence of the target ANT gene and to contain the desired nucleotide change. Introduction of the chimeric oligonucleotide on an extrachromosomal T-DNA plasmid results in efficient and specific ANT gene conversion directed by chimeric molecules in a small number of transformed plant cells. This method is described in Cole-Strauss et al. *Science* 273: 1386–1389 (1996) and Yoon et al. *Proc. Natl. Acad. Sci. USA* 93:2071–2076 (1996).

Other Means for Increasing ANT Activity

One method to increase ANT expression is to use "activation mutagenesis" (see, e.g. Hiyashi et al. *Science* 258: 1350–1353 (1992)). In this method an endogenous ANT gene can be modified to be expressed constitutively, ectopically, or excessively by insertion of T-DNA sequences that contain strong/constitutive promoters upstream of the endogenous ANT gene. As explained below, preparation of transgenic plants overexpressing ANT can also be used to increase ANT expression. Activation mutagenesis of the endogenous ANT gene will give the same effect as overexpression of the transgenic ANT nucleic acid in transgenic plants. Alternatively, an endogenous gene encoding an enhancer of ANT activity or expression of the endogenous ANT gene can be modified to be expressed by insertion of T-DNA sequences in a similar manner and ANT activity can be increased.

Another strategy to increase ANT expression can be the use of dominant hyperactive mutants of ANT by expressing modified ANT transgenes. For example expression of modified ANT with a defective domain that is important for interaction with a negative regulator of ANT activity can be used to generate dominant hyperactive ANT proteins. Alternatively, expression of truncated ANT proteins which have only a domain that interacts with a negative regulator can titrate the negative regulator and thereby increase endogenous ANT activity. Use of dominant mutants to hyperactivate target genes is described in Mizukami et al. *Plant Cell* 8:831–845 (1996).

Inhibition of ANT Activity or Gene Expression

As explained above, ANT activity is important in controlling a number of plant processes through the regulation of cell proliferation. Inhibition of ANT gene expression activity can be used, for instance, to decrease plant organ size/mass or to induce female sterility in plants. In particular, targeted expression of ANT nucleic acids that inhibit endogenous gene expression (e.g., antisense or co-suppression) can be used to inhibit ovule development at early stages and thus induce female sterility. The life span of the transgenic plants can therefore be extended because fertilization (seed formation) can activate and accelerate senescence processes of plants or organs.

Inhibition of ANT gene function can also be used to truncate vegetative growth, resulting in early flowering. Methods that control flowering time are extremely valuable in agriculture to optimize harvesting time as desired. Therefore, by regulating the function of the ANT genes in plants, it is possible to control time of flowering. For instance, acceleration of fertile plant growth can be obtained by expressing ANT antisense RNA during vegetative development to achieve early flowering. Expression of the ANT transgene can then be shut off during reproductive development to get fertile plants.

Inhibition of ANT Gene Expression

The nucleic acid sequences disclosed here can be used to design nucleic acids useful in a number of methods to inhibit ANT or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105:125–149 (1995); Pantopoulos In Progress in Nucleic Acid Research and Molecular Biology, Vol. 48. Cohn, W. E. and K. Moldave (Ed.). Academic Press, Inc.:San Diego, Calif., USA; London, England, UK. p. 181–238; Heiser et al. *Plant Sci.* (Shannon) 127:61–69 (1997)) and by preventing the accumulation of mRNA which encodes the protein of interest, (see, Baulcombe *Plant Mol. Bio.* 32:79–88 (1996); Prins and Goldbach *Arch. Virol.* 141:2259–2276 (1996); Metzlaff et al. *Cell* 88:845–854 (1997), Sheehy et al., *Proc. Nat. Acad. Sci. USA,* 85:8805–8809 (1988), and Hiatt et al., U.S. Pat. No. 4,801, 340).

The nucleic acid segment to be introduced generally will be substantially identical to at least a portion of the endogenous ANT gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress ANT gene expression. The targets can include, for instance, the coding regions, introns, sequences from exon/intron junctions, 5' or 3' untranslated regions, and the like.

Another well known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22:1067–1085 (1993); Flavell *Proc. Natl. Acad. Sci. USA* 91:3490–3496 (1994); Stam et al. *Annals Bot.* 79:3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt ANT gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (Berlin) 75:267–282 (1997)). Triple helix DNAs can be used to target the same sequences identified for antisense regulation.

Catalytic RNA molecules or ribozymes can also be used to inhibit expression of ANT genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature,* 334:585–591 (1988).

Modification of Endogenous ANT Genes

Methods for introducing genetic mutations described above can also be used to select for plants with decreased ANT expression.

Other Means for Inhibiting ANT Activity

ANT activity may be modulated by eliminating the proteins that are required for ANT cell-specific gene expression. Thus, expression of regulatory proteins and/or the sequences that control ANT gene expression can be modulated using the methods described here.

Another strategy is to inhibit the ability of an ANT protein to interact with itself or with other proteins. This can be achieved, for instance, using antibodies specific to ANT. In this method cell-specific expression of ANT-specific antibodies is used to inactivate functional domains through antibody:antigen recognition (see, Hupp et al. *Cell* 83:237–245 (1995)). Interference of activity of an ANT interacting protein(s) can be applied in a similar fashion. Alternatively, dominant negative mutants of ANT can be prepared by expressing a transgene that encodes a truncated ANT protein. Use of dominant negative mutants to inactivate target genes in transgenic plants is described in Mizukami et al. *Plant Cell* 8:831–845 (1996).

Isolation of ANT Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of ANT nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the ANT gene transcript is prepared from the mRNA. Alternatively, cDNA may be prepared from mRNA extracted from other tissues in which ANT genes or homologs are expressed.

The cDNA or genomic library can then be screened using a probe based upon the sequence of a cloned ANT gene disclosed here. Probes may be used to hybridize with genomic DNA or cDNA sequences to isolate homologous genes in the same or different plant species. Alternatively, antibodies raised against an ANT polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the ANT genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), *Academic Press*, San Diego (1990). Appropriate primers and probes for identifying ANT sequences from plant tissues are generated from comparisons of the sequences provided here (e.g. SEQ ID NO:4) and those provided in Klucher et al. and Elliot et al., supra.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence. Because at the very 5' and 3' ends the *Arabidopsis* ANT nucleotide sequence is very similar to the *Brassica* ANT nucleotide sequence but not to other Arabidopsis AP2-domain containing genes, the primers with nucleotide sequences shown in SEQ ID NO:6, SEQ ID NO:7, or SEQ ID NO:8 can be used to screen/isolate ANT orthologs in different species by RT-PCR.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208: 551–565 (1989)), and Gpc2 from maize (GenBank No. U45855, Manjunath et al, *Plant Mol. Biol.* 33:97–112 (1997)).

Alternatively, the plant promoter may direct expression of the ANT nucleic acid in a specific tissue, organ or cell type (ie. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in flowers, ovules, or anthers (particularly the tapetum) are useful in methods in which sterility is desired. An example of a promoter that directs expression in the ovule is the promoter from the BEL1 gene described in Reiser et al. *Cell* 83:735–742 (1995) (GenBank No. U39944). Examples of tapetal-specific promoters include TA29 from tobacco (Mariani et al., *Nature*, 347:737–41 (1990)), and A6 and A9 from *Brassica* (Paul et al., *Plant Mol. Biol.*, 19:611–22, (1992), Hird et a. *Plant Journal*

4:1023–1033 (1993)). Another-specific promoters could also be used such as ones isolated by Twell et al. (*Mol. Gen. Genet.*, 217:240–45, (1991)).

To introduce male sterility, the 2nd and 3rd floral organ (petal and stamens)-specific AP3 promoter (Day, et al., *Development* 121:2887, 1995), for example, can be used. The carpel specific AGL1 (Flanagan and Ma, *Plant J.* 10:343, 1993) or AGL5 (Savidge, et al., *Plant Cell* 7:721, 1995) promoter can be applied for inducing female sterility only. Sterile plants, yet with increased perianth organs, can be obtained by constitutively expressing the ANT gene through AG promoter (Sieburth and Meyerowitz, *Plant Cell* 9:355, 1997) that is active only in reproductive organ primordia and developing male and female organs.

Using the AP1 promoter (Gustafson-Brown, et al., *Cell* 76:131, 1994) that is expressed in floral primordia at early stages of flower development and in developing perianth organs, fertile flowers with enlarged perianth organs can be produced. For the increase of aerial vegetative organ biomass, photosynthetic organ-specific promoters, such as the RBCS promoter (Khoudi, et al., *Gene* 197:343, 1997), can be used. Root biomass can be increased by the constitutive ANT expression under the control of the root-specific ANR1 promoter (Zhang & Forde, *Science*, 279:407, 1998). To increase seed size/mass (an agronomically import trait), seed-specific promoters, such as the LEC promoter (Lotan, et al., *Cell* 93:1195 (1998)), the late-embroygenesis-abundant promoter (West et al. *Plant Cell* 6:173 (1994)), beta-conglycininin alpha-subunit promoter (West et al.), the lectin promoter (Goldberg et al. *Science* 266:605 (1994)), or the Kunitz trypsin inhibitor 3 promoter (Goldberg et al.) can be used. Any strong, constitutive promoters, such as the CaMV 355 promoter, can be used for the increase of total plant biomass.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

The present invention also provides promoter sequences from the ANT gene (SEQ ID NO:3), which can be used to direct expression of the ANT coding sequence or heterologous sequences in desired tissues. ANT is expressed in meristematic cells throughout the plant. ANT promoter sequences of the invention are therefore useful in targeting expression to meristematic cells in lateral roots, leaf primordia, developing leaves, floral primordia, floral organ primordial developing floral organs, ovule primordia, developing ovules, developing embryos, and vascular systems. Genes whose expression can be targeted to these cells in immature organs include disease resistance genes, such as the *Arabidopsis* NPR1 gene (Cao, et al., *Cell* 88:57, 1997) and the nematode resistance locus Gro1 and the *Phytophthora infestans* resistance locus R7 of potato (Leister, et al., *Nature Genetics* 14:421, 1996), for increasing resistance to pathogens and insects in young, sensitive organs.

Because the ANT promoter is expressed in developing embryos at late stages, some genes encoding regulators or key enzymes for biosynthesis of storage oils, proteins, or starches, such as BiP (Hatano, et al., *Plant and Cell Physiology* 38:344, 1997), can be expressed by the control of the ANT promoter.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Chlamydomonas, Chlorella, Citrus, Citrullus, Capsicum, Carthamus, Cocos, Coffea, Cucumis, Cucurbita, Cyrtomium, Daucus, Elaeis, Fragaria, Glycine, Gossypium, Helianthus, Heterocallis, Hordeum, Hyoscyamus, Lactuca, Laminaria, Linum, Lolium, Lupinus, Lycopersicon, Macrocystis, Malus, Manihot, Majorana, Medicago, Nereocystis, Nicotiana, Olea, Oryza, Osmunda, Panieum, Pannesetum, Persea, Phaseolus, Pistachia, Pisum, Pyrus, Polypodium, Prunus, Pteridium, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of ANT mRNA or protein in transgenic plants. Means for detecting and quantitating mRNAs or proteins are well known in the art. The plants of the invention can also be identified by detecting the desired phenotype. For instance, increased biomass of organs or plants can be detected according to well-known techniques. Male or female sterility can be identified by testing for viable pollen and/or the ability to set seed.

The following Examples are offered by way of illustration, not limitation.

EXAMPLE 1

This example shows that increased ANT expression increases cell number and the size/mass of roots, leaves, floral organs, ovules and seeds in *Arabidopsis*.

An ANT cDNA with a BamHI site right before the initiation codon of the ANT coding nucleotide sequence was created by PCR using synthetic oligonucleotide primers. This ANT nucleic acid (from C at 268 to T at 2148 (1881 nucleotides) from SEQ ID NO:1) was ligated at the BglII site of the plasmid vector pMON530 (Rogers, et al., *Meth. Enzymol.* 153:253, 1987) under the constitutive 35S promoter, and the recombinant plasmid DNA which has an insert of the ANT cDNA in the sense direction with respect to the CaMV 35S promoter (35S::ANT) were selected. *Agrobacterium* cells were transformed with the recombinant plasmid DNA, and used for *Agrobacterium*-mediated plant transformation by vacuum infiltration with *Arabidopsis* plants (Col-0 ecotype). $T_1$ seeds were collected from transformed plants about three weeks after vacuum infiltration, and planted on MS plates with kanamycin for screening $T_1$ transgenic seedlings.

$T_1$ seeds include oversized seeds, which were distinguished because they did not pass through a mesh of defined size. The majority of these seeds were kanamycin resistant, carrying the 35S::ANT transgene. This phenotype was not observed in vector only controls.

Multiple $T_1$ seedlings were larger than vector only control transgenic seedlings. As they develop, $T_1$ plants produced a highly branched root system having a larger mass than vector only controls. In addition, the plants had enlarged leaves, floral organs, and ovules as compared to the vector only controls. For example, the average flower and leaf biomass of $T_1$ lines was approximately three times and 2.5 times that of the vector only control, respectively. DIC microscopy and scanning electron microscopy revealed that this enlarged organ phenotype of $T_1$ plants was due to the increased cell number in the organs. In addition, $T_1$ plants were sterile. Preliminary examination suggests that anthers fail to shed pollen (which are morphologically normal) and the ovules were unusually large with an increased number of nucellar cells that compress/displace the female gametophyte.

Because sterility made it difficult to generate and propagate homozygous transgenic lines, we used a chemical induction system as described by Aoyama, and Chua *Plant J.* 11:605–612 (1997) and McNellis et al. *Plant J.* 14:247–257 (1998) to regulate ectopic ANT transcription. This system utilizes a chimeric transcription factor gene (35S::GVG), consisting of the 35S promoter, the DNA-binding domain of the yeast transcription factor GAL4, a transactivating domain, and the receptor domain of the glucocorticoid receptor (GR). The ANT gene was inserted downstream from a promoter (UAS::ANT) containing the binding site for the GVG transcription factor. The 35S::GVG/UAS::ANT construct was introduced into wild-type *Arabidopsis* and fertile transgenic lines were obtained generally as described above.

Transgenic $T_2$ plants were germinated on MS agar plates and transferred to plates either with or without the chemical inducer, dexamethasone (DEX), a synthetic glucocorticoid hormone that binds and activates the GVG transcription factor. Multiple transgenic lines were obtained that displayed an enlarged leaf phenotype after treatment with DEX. The increase in organ size/mass is due to an increased number of cells. DEX had no effect on control transgenic plants with only the 35S::GVG/UAS vector. Taken together, these results suggest that ectopic ANT expression increases organ size/mass by increasing cell number.

EXAMPLE 2

This example shows that essentially the same phenotypic changes observed in *Arabidopsis* were observed in tobacco.

For generating tobacco transgenic plants expressing ANT cDNA under the control of the constitutive 35S promoter, the above recombinant plasmid DNA was used for *Agrobacterium*-mediated tobacco callus transformation. Tobacco calli were induced from sterilized tobacco leaf (SR1 variety) placed on callus-inducing plates, then co-cultivated with *Agrobacterium* cells carrying the above recombinant DNA for three days. After washing bacterial cells out, leaf calli were placed on shoot-inducing agar plate containing kanamycin and carbenicillin to generate transformed shoots. These $R_0$ shoots were transferred on root inducing agar plates, then transplanted on soil after regeneration of roots.

The $R_0$ plants in which the ANT gene was constitutively expressed under the control of the CaMV 35S promoter produced wider leaves (about 1.5 times that of vector only control transgenic plants), relatively larger flowers (about 1.7 time greater mass than vector only control transgenic plants), and sterility as observed with *Arabidopsis*. The sterility is largely caused by the failure of dehiscence of anthers as seen in the *Arabidopsis* transgenic anthers. Some $R_0$ plants produced functional pollen grains in their closed anthers, and produced seeds ($R_1$ seeds) upon self-pollination by hand using pollen grains dissected from the anther. These $R_1$ seeds had mass about 1.5 times that of seed from vector only control plants.

EXAMPLE 3

This example describes plant organ size/mass reduction and altered flowering by co-suppressing endogenous gene activity by the ANT transgene in *Arabidopsis* and tobacco.

*Arabidopsis* $T_1$ lines described above included lines exhibiting reduced organ size/mass and organ cell numbers. These plants were completely or partially female sterile, as are loss-of-function ant mutants. In these lines, expression of ANT mRNA was highly reduced, suggesting that co-suppression of the endogenous ANT gene, as well as that of the ANT cDNA, took place in the lines. From partially sterile $T_1$ lines, transgenic $T_2$ plants were obtained that segregated for the same co-suppressed phenotype as in $T_1$ parental plants.

Reduction of organ size/mass was also observed in co-suppressed $R_0$ tobacco plants.

Multiple co-suppressed lines also exhibited early flowering. Plants of these lines displayed reduced numbers of rosette leaves and fewer days before bolting. Because early-flowering phenotype was not observed in loss-of-function ant mutants, co-suppression by the ANT transgene could also influence other unknown ANT related genes that regulate flowering time by itself or together with ANT. Similar results were also observed in co-suppressed transgenic tobacco plants.

EXAMPLE 4

This example shows that loss of ANT function reduces mature organ size by decreasing cell numbers.

Because ANT mRNA accumulated in leaf (Elliott, R. C., et al. (1996) *Plant Cell* 8:155–168), we examined the effect of a loss-of-function ant mutation on vegetative shoot development. While there was no difference in the timing of leaf primordia initiation or the number of leaf primordia between ant-1 and control wild-type plants (not shown), the width and length of mature ant-1 leaves were both reduced in comparison with those of corresponding wild-type leaves. Because ant mutant floral organs were found to be reduced in size (Klucher, K. M., et al. (1996) *Plant Cell* 8:137–153; Elliott, R. C., et al. (1996) *Plant Cell* 8:155–168), these observations demonstrate that loss of ANT function reduces organ size throughout shoot development.

A change in organ size can reflect an alteration in the size or number of cells, or both. To understand why ant-1 organs are smaller, we examined the size and number of cells in mature ant-1 organs and compared them with those in wild-type controls. The distal portion of the petal epidermis was observed initially because it has cells that are diploid and uniform in size and shape. We found that ant-1 organs had fewer cells per unit area and per organ than wild type, however ant-1 cells were much larger than normal. Essentially the same phenotype was observed in the epidermis and subdermal cell-layers of all ant-1 floral organs and leaves. Thus, systemic reduction in size of ant-1 organs is associated with a decrease in cell number, but not a decrease in cell size.

Because ant mutants reduce the number of floral organs, it has been suggested that ANT might be involved in organ primordium patterning as well as organ growth. To evaluate this possibility, we observed the pattern of sepal primordia in developing wild type and ant-I floral buds under SEM. By the end of floral stage 4 (Smyth, D. R., et al. (1990) *Plant Cell* 2:755–767), all four sepal primordia were initiated at the periphery of developing wild-type floral buds. In ant-1 floral buds at the comparable stage, the organ primordia initiated were arranged normally in ant-1 floral buds, although the number of floral organ was reduced (not shown). Thus, ANT appears to have little role in controlling the position of floral organ primordium in developing floral buds.

EXAMPLE 5

This example shows the isolation of an ANT ortholog from *Brassica napus* (Canola).

The nucleic acid sequence and the encoded protein of the *Brassica* cDNA are shown in SEQ ID NO:4 and SEQ ID NO:5 respectively.

To prepare this nucleic acid, total RNA was isolated from young shoot apices of *Brassica napus* (Canola) seedlings using TRIZOL as described by Colasanti et al. (*Cell.* 93:593–603 (1998)). cDNA was made by reverse transcription, and amplified by PCR using the high fidelity thermotolerant DNA polymerase PFU and oligonucleotide primers. The primers had the initiation codon and the anti-parallel nucleotide sequence downstream of the stop codon of the *Arabidopsis* ANT nucleotide sequence, respectively. The PCR products were subcloned into an *E. coli* vector and screened by PCR using different sets of oligonucleotide primers having internal ANT nucleotide sequence. Nucleotide sequence of the inserted *Brassica* DNA of selected recombinant plasmid clones was determined and compared to the *Arabidopsis* ANT nucleotide sequence for confirmation. The *Brassica* ANT (BANT) gene shares 85.5% identity to the *Arabidopsis* ANT gene in their coding region at the nucleotide level and the BANT polypeptide sequence is 83.7% identical to the ANT polypeptide sequence, respectively.

EXAMPLE 6

This example shows use of the ANT 5'-upstream nucleotide sequence (promoter) for expressing heterologous genes in meristematic cells.

A HindIII-BglII fragment which includes the correctly oriented ANT promoter was inserted into the pBI101 plasmid vector DNA (CLONTECH) at the HindIII and BamHI sites which are located right before the initiation codon of the GUS (beta-glucuronidase) gene. The same fragment was also inserted into the plasmid pBIN m-gfp5-ER (Haseloff, et al., *Proc. Natl. Acad. Sci. U.S.A.* 94:2122–2127, (1997) at the HindIII-BamHI sites located immediately before the initiation codon of the GFP (green fluorescence protein) gene. *Arabidopsis* wild-type plants were transformed by these recombinant plasmids using the *Agrobacterium*-mediated vacuum infiltration method. Multiple $T_1$ lines, and their following generations, exhibited GUS activity or GFP expression in meristematic cells throughout plant development as expected, proving that the ANT promoter is useful for expressing a heterologous gene in meristematic cells.

EXAMPLE 7

This example shows activation of the cyclin D3 (CYCD3) gene expression by increasing ANT gene expression in *Arabidopsis* plants.

Cell proliferation is directly controlled by the activity of cell cycle regulatory genes, such as cyclins and cdks (Nasmyth, *Trends Genet.,* 12:405–412, (1996); Morgan, *Nature,* 374:131–134, 1995; and Burssens, et al., *Plant Physiol. Biochem.,* 36:9–19, (1998)). Because organs from $T_1$ transgenic lines in which ANT gene expression is controlled by the CaMV 35S promoter had increased number of cells, and thus increased cell proliferation activity, expression of cyclin genes in young and mature organs of $T_1$ plants was measured by quantitative RT-PCR analysis. In young developing organs, where cell proliferation was observed in both 35S::ANT and control plants, the difference of expression levels of cyclin genes between them were not significant. However, in mature organs, while mRNA accumulation of CYCD3, which encodes a key regulator for G1/S entry in the *Arabidopsis* cell cycle (Soni, et al., *Plant Cell.* 7:85–103 (1995); Fuerst, et al., *Plant Physiol.* 112:1023–1033 (1996), is no longer detected in control, it was detected in 35S::ANT lines. These results agree with observations that no growth differences were detected at early stages of organ development between 35S::ANT lines and control lines; however, when organs of control plants were mature and ceased cell proliferation, cells in the same aged organs of 35S::ANT plants continued to proliferate and give rise to enlarged organs as the result.

This result demonstrates that the increased constitutive ANT activity directly and/or indirectly controls the cell cycle machinery via regulating expression of a cell cycle regulator gene(s) and continuously activating cell proliferation in developing organs. This also indicates that certain genes involved in cell cycle machinery are targets of the ANT transcription factor gene (Klucher et al. and Elliot et al.). Taken together, these results suggest that modulation of expression of these ANT-target genes could regulate organ size/mass and fertility in plants.

EXAMPLE 8

This example shows that ectopic expression of BANT, an ANT ortholog from Brassica napus (Canola), increases organ mass/size in Arabidopsis.

The Brassica ANT (BANT) cDNA, which has the nucleic acid sequence shown in SEQ ID NO:4, was inserted into the plasmid vector pMON530 (Rogers, et al., Method. Ezymol. 153:253, 1987) under the constitutive 35S promoter in the sense direction. The recombinant plasmid DNA was used for Agrobacterium transformation, and the Agrobacterium cells transformed with the 35S::BANT plasmid DNA was used for Agrobacterium mediated plant transformation by vacuum infiltration with Arabidopsis plants (Col-0 ecotype). $T_1$ seeds were collected about three weeks after vacuum infiltration, and planted on MS agar plates with kanamycin for screening $T_1$ transgenic seedlings.

$T_1$ plants ectopically expressing the 35S::BANT transgene exhibited multiple organ hyperplasia, as seen in 35S::ANT transgenic plants described above (Example 1). That is, leaves and floral organs were, at most, three times larger than control organs. These transgenic plants were essentially male sterile, and are often female sterile as well. Some plants, however, produced seeds upon fertilization with wild-type pollen grains by hand-pollination, and the $T_2$ seeds exhibited increased mass/size. The kanamycin-resistant $T_2$ seedlings developed into plants displaying the same phenotype as the $T_1$ plants, suggesting that the effect of ANT ectopic expression is heritable.

EXAMPLE 9

This example shows increased ANT expression induces asexual reproduction and formation of adventitious shoots, organs, and embryos in Arabidopsis plants.

Fully matured stems or organs, such as leaves, were dissected from $T_1$ plants ectopically expressing ANT and placed in water or on MS agar plates without any phytohormones. After about two-week incubation, adventitious root formation was observed at the cut surface of stems or leaves. Occasionally, adventitious roots were also produced from the leaf surface. This adventitious root formation was never observed control stems or leaves treated in the same way.

Excised inflorescence (flowering) stems from fully matured $T_1$ plants ectopically expressing ANT were placed on MS agar plates without phytohormones for 10 days. Adventitious root formation was observed in the cut surface of stems, while adventitious shoot formation was observed in the senesced floral buds. These shoots eventually produced roots as well, developing into complete plants that exhibited the same transgenic trait (enlarged organ size/mass) as the original plants. The control inflorescence stems did not show any activity of asexual reproduction under the same conditions.

Similar asexual reproduction was observed in embryos excised from developing 35S::ANT transgenic seeds. The late torpedo-stage to nearly mature embryos were excised from developing green seeds, and grew on phytohormone-free MS agar plates containing 50 μg/ml kanamycin. Although these embryos developed into seedlings, some cells reproduced secondary embryos or adventitious shoots, which also developed into complete plants. The control embryos did not propagate asexually under the same conditions.

CONCLUSION

In higher plants intrinsic organ size is determined genetically, although it can be influenced greatly by environmental factors. The size of organs reflects the number and size of cells. The total cell number of an organ is determined by the proliferation of undifferentiated meristematic cells that are competent to divide. During shoot development, lateral organs are initiated as primordia from apical and lateral meristems. While most cells in organ primordia are meristematic and proliferate, cells lose meristematic competence and withdraw from the cell cycle as organs develop. Thus, the maintenance of meristematic competence of cells is a key mechanism that mediates organ growth and cell proliferation by defining total cell numbers, and thereby the size of plant organs. However, the molecular nature of meristematic competence and the developmental regulators that control meristematic competence are not well understood.

The Arabidopsis ANT gene encodes a transcription factor of the AP2-domain family that has been found only in plant systems. ANT mRNA accumulates in primordia of all lateral shoot organs and diminishes as organs develop. This suggests that ANT may have a general function in organ growth. Consistent with ANT expression in leaf primordia and undifferentiated growing leaves, it was found that all mature leaves of the loss-of-function ant-1 mutant were reduced in size in comparison with corresponding wild-type leaves. Because ant-1 floral organs were also smaller than normal, ANT is most likely required for organ growth throughout post-embryonic shoot development. Organ size can be influenced by cell size, cell number, or both. It was found that ant-1 organs had fewer cells per unit area and per organ than wild type, however ant-1 cells were much larger than normal. This demonstrates that the systemic reduction in size of ant-1 organs is the result of a decrease in cell number, but not a decrease in cell size. Therefore, ANT function is necessary to attain the intrinsic cell number of plant organs.

The experiments described here demonstrate that ectopic ANT expression is sufficient to increase organ size and mass by enhancing organ growth that is coordinated with organ morphogenesis in Arabidopsis plants. Differentiated cells in fully mature 35S::ANT petals were the same size as those in wild-type petals. Similarly, no obvious difference in cell size was detected in the epidermis between control and 35S::ANT organs other than petals. Thus, an increase of cell numbers, and not cell size, is primarily responsible for the enlarged 35S::ANT organs. Similar loss- and gain-of-function effects on organ size was observed when plants were grown plants grown under short-day, continuous-light conditions, and in poor or rich media. Thus, ANT function seems to be independent of the perception of external growth signals. In contrast to the striking effects on final organ size, ectopic ANT expression did not perceptibly alter the size or structure of apical and lateral meristems, nor did it change the size or number of organ primordia. Although loss of ANT function reduced the number of floral organs, the organ primordia initiated were arranged and sized normally in ant-1 floral buds. Therefore, ANT does not determine organ primordium size, and most likely does not influence organ primordium number by controlling the organization of the apical and lateral meristems.

How does ANT control cell numbers during organogenesis? In general, plant organ growth involves neither cell migration nor cell death; thus, organ cell number essentially depends on proliferation of the meristematic cells in developing organ. Because ANT is expressed in meristematic cells of the developing organs, it might modulate cell proliferation during organogenesis and thereby determine the total cell number in mature organs. To test this idea, the extent of cell proliferation in control and ant-1 organs was tested by measuring cell numbers and cell size of both developing and fully mature petals. During mid-floral stage 9, the adaxial epidermal cells of wild-type petals were not differentiated and divided frequently, whereas ant-1 petals had fewer undifferentiated cells than normal per unit area and per organ. This reduction in cell numbers became more pronounced in fully differentiated ant-1 petals at stage 15. Thus, there are fewer cell divisions than normal in ant-1 petals throughout organogenesis, particularly during later developmental stages prior to maturation. Cell growth occurred without cell division in ant-1 petals, resulting in extremely large cells.

These results suggest that ANT is required for the normal extent of cell proliferation, but not primarily for cell growth. To understand how ANT regulates the extent of cell proliferation, we studied how ectopic ANT expression affects organ size, cell size, and cell numbers during petal development. In contrast to the early effect on cell numbers in ant-1 petals, cell numbers and cell size in 35S::ANT petals at stage 9 were normal. This demonstrates that ectopic ANT expression does not increase cell growth or the frequency of cell proliferation in developing petals during early stages, and suggests that increased ANT activity does not alter the intrinsic cell cycle time. By stage 15, however, the total cell number of fully mature 35S::ANT petals reached approximately 2.5 times that of controls, indicating that additional cell divisions occurred in 35S::ANT petals prior to organ maturation, yet only after stage 9. Extra cell divisions must be coordinated with cell growth, since cell size in mature 35S::ANT petals is normal. Therefore, it is likely that ectopic ANT expression allows petal cells to proliferate for a longer period than normal without altering the intrinsic cell cycle time. Similar results were obtained when comparing growth of rosette leaves of 35S::ANT and control seedlings. At 16 days after germination (16 DAG), both 35S::ANT and control seedlings had the same number of rosette leaves, and all leaves of 35S::ANT seedlings were the same size as corresponding control leaves. However, 35S::ANT leaves continued to grow beyond the period in which corresponding control leaves ceased to grow, eventually giving rise to larger leaves than normal. This observation supports the hypothesis that prolonged cell proliferation coordinated with cell growth causes hyperplasia in 35S::ANT plants. Taken together, these observations suggests that ANT regulates the period of cell proliferation by maintaining meristematic competence of cells during organogenesis. The results presented here also suggest that ANT does not influence CycD3 expression in tissue where most cells are meristematic. Similar results were obtained in comparing mRNA levels of CycB1b (Cyc1bAt), a mitotic cyclin gene. Hence, ANT maintains the meristematic competence of cells, and consequently sustains expression of cell cycle regulators.

Another striking finding that connects ANT function with the maintenance of meristematic competence is neoplasia found in the *Arabidopsis* 35S::ANT organs. That is, clusters of undifferentiated cells i.e., calli) were generated from wounds or senesced-surfaces of 35:ANT plants, or detached-ends of fully differentiated 35S::ANT organs without external phytohormone treatment. These calli often differentiated into organs, such as roots, leaves, or shoots. This neoplasia was observed consistently in 35S::ANT organs, but never was seen in control organs treated in the same way. It is well established that differentiated plant tissue can induce calli after phytohormone treatment. Ectopic ANT expression in differentiated cells that are normally quiescent preserves meristematic competence and decreases their dependence on phytohormones for reentry into the cell cycle.

The findings presented here demonstrate ANT is an intrinsic organ size regulator that influences organ growth and the period of cell proliferation during organogenesis. In a proposed model of ANT action in plant organ size regulation, developmental growth signals activate growth regulators, which positively regulate ANT during organogenesis. ANT functions to maintain meristematic competence of cells, thereby modulating the expression of cell cycle and cell growth regulators. As a result, ANT sustains cell proliferation that is coupled to cell growth in developing organs. Ectopically expressed ANT, therefore, results in the abnormal retention of meristematic competence of cells and causes hyperplasia and neoplasia, while the absence of ANT causes precocious termination of cell proliferation and organ growth. In plant and animal systems, growth signaling pathways and the cell cycle machinery appear to share many common factors. Nevertheless, given the immobile attributes of plant life and plant cells, which are surrounded by rigid cell walls, some aspects of plant growth and cell proliferation are likely to be regulated and coordinated in a different way from those of animals. Thus, it may not be surprising that ANT is a plant specific regulator, and identification of upstream regulators and downstream targets of ANT may reveal how plants uniquely coordinate cell proliferation with pattern formation to control organ size. It has been suggested that the genetic basis for plant interspecies diversity of phenotype might be minor changes in the structure or expression of orthologous regulatory genes. Hence, differences in structure and expression pattern of ANT and its orthologs, at least in part, may be a mechanism that is responsible for the interspecies diversity of organ size in higher plants. Finally, increasing organ mass by ectopic ANT expression might be a new method for improving the yield of agriculturally important plants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A method of directing expression of a heterologous nucleic acid in a meristematic cell(s) of a plant, the method comprising introducing into the plant an expression cassette comprising an ANT promoter operably linked to a heterologous polynucleotide, wherein the ANT promoter is as shown in SEQ ID NO: 3.

2. An isolated nucleic acid molecule comprising an ANT promoter sequence as shown in SEQ ID NO: 3.

3. The isolated nucleic acid molecule of claim 1, further comprising a heterologous polynucleotide operably linked to the ANT promoter sequence.

* * * * *

SEQUENCE LISTING

<160> NUMBER OF SEQ ID NOS: 8

<210> SEQ ID NO 1
<211> LENGTH: 2148
<212> TYPE: DNA
<213> ORGANISM: Arabidopsis thaliana
<220> FEATURE:
<221> NAME/KEY: CDS
<222> LOCATION: (269)..(1936)
<223> OTHER INFORMATION: AINTEGUMENTA (ANT) cDNA
<223> OTHER INFORMATION: AINTEGUMENTA (ANT)

<400> SEQUENCE: 1

```
agatcccaac ggattcaaac agcaaatttg tgctttgctc ttctctctta ttataatatc      60
ctctcaaaaa ccctctccta tatcctccta agccccccct tccttgtttc tctaccgcaa     120
caaagaaaaa acaaaagttt gagaaaaatg gtgtgttcgt tgtgtaacca atgattgggt     180
tttagcttac tacttcgaga gattataaga aagaaagagt gaagatacat tatagaaaga     240
agagaagcag aaaccaaaaa aagaaaacc atg aag tct ttt tgt gat aat gat      292
                                 Met Lys Ser Phe Cys Asp Asn Asp
                                  1               5 gat aat aat cat agc aac acg act aat ttg tta ggg ttc tca ttg tct      340
Asp Asn Asn His Ser Asn Thr Thr Asn Leu Leu Gly Phe Ser Leu Ser
    10                  15                  20 tca aat atg atg aaa atg gga ggt aga gga ggt aga gaa gct att tac      388
Ser Asn Met Met Lys Met Gly Gly Arg Gly Gly Arg Glu Ala Ile Tyr
 25                  30                  35                  40 tca tct tca act tct tca gct gca act tct tct tct tct gtt cca cct      436
Ser Ser Ser Thr Ser Ser Ala Ala Thr Ser Ser Ser Ser Val Pro Pro
                 45                  50                  55 caa ctt gtt gtt ggt gac aac act agc aac ttt ggt gtt tgc tat gga      484
Gln Leu Val Val Gly Asp Asn Thr Ser Asn Phe Gly Val Cys Tyr Gly
             60                  65                  70 tct aac cca aat gga gga atc tat tct cac atg tct gtg atg cca ctc      532
Ser Asn Pro Asn Gly Gly Ile Tyr Ser His Met Ser Val Met Pro Leu
         75                  80                  85 aga tct gat ggt tct ctt tgc tta atg gaa gct ctc aac aga tct tct      580
Arg Ser Asp Gly Ser Leu Cys Leu Met Glu Ala Leu Asn Arg Ser Ser
     90                  95                 100 cac tcg aat cac cat caa gat tca tct cca aag gtg gag gat ttc ttt      628
His Ser Asn His His Gln Asp Ser Ser Pro Lys Val Glu Asp Phe Phe
105                 110                 115                 120 ggg acc cat cac aac aac aca agt cac aaa gaa gcc atg gat ctt agc      676
Gly Thr His His Asn Asn Thr Ser His Lys Glu Ala Met Asp Leu Ser
                125                 130                 135 tta gat agt tta ttc tac aac acc act cat gag ccc aac acg act aca      724
Leu Asp Ser Leu Phe Tyr Asn Thr Thr His Glu Pro Asn Thr Thr Thr
            140                 145                 150 aac ttt caa gag ttc ttt agc ttc cct caa acc aga aac cat gag gaa      772
Asn Phe Gln Glu Phe Phe Ser Phe Pro Gln Thr Arg Asn His Glu Glu
        155                 160                 165 gaa act aga aat tac ggg aat gac cct agt ttg aca cat gga ggg tct      820
Glu Thr Arg Asn Tyr Gly Asn Asp Pro Ser Leu Thr His Gly Gly Ser
    170                 175                 180 ttt aat gta ggg gta tat ggg gaa ttt caa cag tca ctg agc tta tcc      868
Phe Asn Val Gly Val Tyr Gly Glu Phe Gln Gln Ser Leu Ser Leu Ser
185                 190                 195                 200 atg agc cct ggg tca caa tct agc tgc atc act ggc tct cac cac cac      916
Met Ser Pro Gly Ser Gln Ser Ser Cys Ile Thr Gly Ser His His His
```

```
                      205                 210                 215
caa caa aac caa aac caa aac cac caa agc caa aac cac cag cag atc    964
Gln Gln Asn Gln Asn Gln Asn His Gln Ser Gln Asn His Gln Gln Ile
        220                 225                 230 tct gaa gct ctt gtg gag aca agc gtt ggg ttt gag acg acg aca atg   1012
Ser Glu Ala Leu Val Glu Thr Ser Val Gly Phe Glu Thr Thr Thr Met
    235                 240                 245 gcg gct gcg aag aag aag agg gga caa gag gat gtt gta gtt gtt ggt   1060
Ala Ala Ala Lys Lys Lys Arg Gly Gln Glu Asp Val Val Val Val Gly
250                 255                 260 cag aaa cag att gtt cat aga aaa tct atc gat act ttt gga caa cga   1108
Gln Lys Gln Ile Val His Arg Lys Ser Ile Asp Thr Phe Gly Gln Arg
265                 270                 275                 280 act tct caa tac cga ggc gtt aca aga cat aga tgg act ggt aga tat   1156
Thr Ser Gln Tyr Arg Gly Val Thr Arg His Arg Trp Thr Gly Arg Tyr
                285                 290                 295 gaa gct cat cta tgg gac aat agt ttc aag aag gaa ggt cac agt aga   1204
Glu Ala His Leu Trp Asp Asn Ser Phe Lys Lys Glu Gly His Ser Arg
            300                 305                 310 aaa gga aga caa gtt tat ctg gga ggt tat gat atg gag gag aaa gct   1252
Lys Gly Arg Gln Val Tyr Leu Gly Gly Tyr Asp Met Glu Glu Lys Ala
        315                 320                 325 gct cga gca tat gat ctt gct gca ctc aag tac tgg ggt ccc tct act   1300
Ala Arg Ala Tyr Asp Leu Ala Ala Leu Lys Tyr Trp Gly Pro Ser Thr
    330                 335                 340 cac acc aat ttc tct gcg gag aat tat cag aaa gag att gaa gac atg   1348
His Thr Asn Phe Ser Ala Glu Asn Tyr Gln Lys Glu Ile Glu Asp Met
345                 350                 355                 360 aag aac atg act aga caa gaa tat gtt gca cat ttg aga agg aag agc   1396
Lys Asn Met Thr Arg Gln Glu Tyr Val Ala His Leu Arg Arg Lys Ser
                365                 370                 375 agt ggt ttc tct agg ggt gct tcc atc tat aga gga gtc aca aga cat   1444
Ser Gly Phe Ser Arg Gly Ala Ser Ile Tyr Arg Gly Val Thr Arg His
            380                 385                 390 cac cag cat gga agg tgg caa gca cgg att ggt aga gtc gct gga aac   1492
His Gln His Gly Arg Trp Gln Ala Arg Ile Gly Arg Val Ala Gly Asn
        395                 400                 405 aaa gat ctc tac ctt gga act ttt gga acc caa gaa gaa gct gca gaa   1540
Lys Asp Leu Tyr Leu Gly Thr Phe Gly Thr Gln Glu Glu Ala Ala Glu
    410                 415                 420 gct tac gat gta gca gca att aag ttc cgt ggc aca aat gct gtg act   1588
Ala Tyr Asp Val Ala Ala Ile Lys Phe Arg Gly Thr Asn Ala Val Thr
425                 430                 435                 440 aac ttt gat atc acg agg tac gat gtt gat cgt atc atg tct agt aac   1636
Asn Phe Asp Ile Thr Arg Tyr Asp Val Asp Arg Ile Met Ser Ser Asn
                445                 450                 455 aca ctc ttg tct gga gag tta gcg cga agg aac aac aac agc att gtc   1684
Thr Leu Leu Ser Gly Glu Leu Ala Arg Arg Asn Asn Asn Ser Ile Val
            460                 465                 470 gtc agg aat act gaa gac caa acc gct cta aat gct gtt gtg gaa ggt   1732
Val Arg Asn Thr Glu Asp Gln Thr Ala Leu Asn Ala Val Val Glu Gly
        475                 480                 485 ggt tcc aac aaa gaa gtc agt act ccc gag aga ctc ttg agt ttt ccg   1780
Gly Ser Asn Lys Glu Val Ser Thr Pro Glu Arg Leu Leu Ser Phe Pro
    490                 495                 500 gcg att ttc gcg ttg cct caa gtt aat caa aag atg ttc gga tca aat   1828
Ala Ile Phe Ala Leu Pro Gln Val Asn Gln Lys Met Phe Gly Ser Asn
505                 510                 515                 520 atg ggc gga aat atg agt cct tgg aca tca aac cct aat gct gag ctt   1876
```

```
Met Gly Gly Asn Met Ser Pro Trp Thr Ser Asn Pro Asn Ala Glu Leu
            525                 530                 535 aag acc gtc gct ctt act ttg cct cag atg ccg gtt ttc gct gct tgg    1924
Lys Thr Val Ala Leu Thr Leu Pro Gln Met Pro Val Phe Ala Ala Trp
        540                 545                 550 gct gat tct tga tcaacttcaa tgactaactc tggttttctt ggtttagttg         1976
Ala Asp Ser
        555 ctaagtgttt tggtttatct ccggttttat ccggtttgaa ctacaattcg gtttagtttc   2036 gtcggtataa atagtatttg cttaggagcg gtatatgttt cttttgagta gtattcatgt   2096 gaaacagaat gaatctctct ataacatatt attttaatga atctccttttg ct          2148

<210> SEQ ID NO 2
<211> LENGTH: 555
<212> TYPE: PRT
<213> ORGANISM: Arabidopsis thaliana
<220> FEATURE:
<223> OTHER INFORMATION: AINTEGUMENTA (ANT)

<400> SEQUENCE: 2

Met Lys Ser Phe Cys Asp Asn Asp Asp Asn Asn His Ser Asn Thr Thr
  1               5                  10                  15

Asn Leu Leu Gly Phe Ser Leu Ser Ser Asn Met Met Lys Met Gly Gly
             20                  25                  30

Arg Gly Gly Arg Glu Ala Ile Tyr Ser Ser Ser Thr Ser Ser Ala Ala
         35                  40                  45

Thr Ser Ser Ser Ser Val Pro Pro Gln Leu Val Gly Asp Asn Thr
     50                  55                  60

Ser Asn Phe Gly Val Cys Tyr Gly Ser Asn Pro Asn Gly Gly Ile Tyr
 65                  70                  75                  80

Ser His Met Ser Val Met Pro Leu Arg Ser Asp Gly Ser Leu Cys Leu
                 85                  90                  95

Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
        115                 120                 125

His Lys Glu Ala Met Asp Leu Ser Leu Asp Ser Leu Phe Tyr Asn Thr
    130                 135                 140

Thr His Glu Pro Asn Thr Thr Thr Asn Phe Gln Glu Phe Phe Ser Phe
145                 150                 155                 160

Pro Gln Thr Arg Asn His Glu Glu Glu Thr Arg Asn Tyr Gly Asn Asp
                165                 170                 175

Pro Ser Leu Thr His Gly Gly Ser Phe Asn Val Gly Val Tyr Gly Glu
            180                 185                 190

Phe Gln Gln Ser Leu Ser Leu Ser Met Ser Pro Gly Ser Gln Ser Ser
        195                 200                 205

Cys Ile Thr Gly Ser His His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255

Gln Glu Asp Val Val Val Val Gly Gln Lys Gln Ile Val His Arg Lys
            260                 265                 270

Ser Ile Asp Thr Phe Gly Gln Arg Thr Ser Gln Tyr Arg Gly Val Thr
```

```
                275                 280                 285
Arg His Arg Trp Thr Gly Arg Tyr Glu Ala His Leu Trp Asp Asn Ser
    290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
                340                 345                 350

Tyr Gln Lys Glu Ile Glu Asp Met Lys Asn Met Thr Arg Gln Glu Tyr
                355                 360                 365

Val Ala His Leu Arg Arg Lys Ser Ser Gly Phe Ser Arg Gly Ala Ser
    370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
                420                 425                 430

Phe Arg Gly Thr Asn Ala Val Thr Asn Phe Asp Ile Thr Arg Tyr Asp
    435                 440                 445

Val Asp Arg Ile Met Ser Ser Asn Thr Leu Leu Ser Gly Glu Leu Ala
    450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
                500                 505                 510

Asn Gln Lys Met Phe Gly Ser Asn Met Gly Gly Asn Met Ser Pro Trp
    515                 520                 525

Thr Ser Asn Pro Asn Ala Glu Leu Lys Thr Val Ala Leu Thr Leu Pro
    530                 535                 540

Gln Met Pro Val Phe Ala Ala Trp Ala Asp Ser
545                 550                 555

<210> SEQ ID NO 3
<211> LENGTH: 4228
<212> TYPE: DNA
<213> ORGANISM: Arabidopsis thaliana
<220> FEATURE:
<223> OTHER INFORMATION: ANT gene 5' promoter

<400> SEQUENCE: 3
gtcgactcta ggcctcactg gcctaatacg actcactata gggagctcga ggatccttta    60
gttagaaaaa actttctttg tacgtgtgtg tgtgtgtttt aagttcaatt ataactagtc   120
acatgtgata tcacaatata tatattgaaa ttggaattat tcatattaat gagttagcat   180
taatatatat acgctgacat taccaaccaa atgtttctgc ttttatggat agttctatat   240
gttgcacttg attatagata ctatataaaa ctgggtttta ttaaaatccg tacccataac   300
aaaagtggac caaaacgaga tccatggttt tgtgtttact ttgttggtta accagataat   360
atgattatgg aagattaaat ctttactaaa ttataaaata atttggaaaa acaaacttaa   420
atatgttgag tgtcttcagt gctcactgtt caagaataat ctcgtgttat cctacttgaa   480
```

-continued

```
ctagaagttg atatacataa acacgtgaat attttaacga ccgtacataa acacatgtat      540
cgatcaaata caaattatta tgagactaga atccaagatg aggatgactc tagcagaata      600
tacacagcta agaatttgta caagagagtc gaaaaataga ttctaatcat ttaaaaaaga     660
tatggatttc agttacggat tgatattacc attacgcagt agtacataca cataatttt       720 tgttttgtt ttaccgataa tagaatgaaa atgttgtgtt aaaatattg gttttactaa         780 aactcgtttt atgttaacta tataatgtct ttccgcatgt aaattgaaac aaaactgtaa     840
tacaaattat gttaagccat tgcaattaaa aaatccacgg gtagtaaatc ctcagaagat     900
tatgttaagt ctacaaattt tctctttaga ttagtaaggt ttgagacaaa attatgtata     960
ccttgcaggg gtataaaggt cactgcatag tcagactcag catgaagcca aagagtcgtc   1020
tctgtcctaa agatatctac agctgcttcg cctgtgaata gagaagaaat tgaatgatga   1080
gagatcccat ctagcgtttc acgtttgcgt tctccgtcgc aactttggcg gttgttgact   1140 tttttttctta tgtcgttgtt tgactaattt tctcagagtg agagtgtaat caagaaaact    1200
aatattcgaa agaaagaaa aaaaggcaa gaaaactatt gtcgaaaaga cataaatgac     1260
actaaaattg gattattaaa aatggtatat atgtttggtg gaatttataa tcattaccaa       1320
aatcaaagga aggagagagg gacctcttcg tgcttatgat ttccctccta aacaactgct    1380
cccactatcc ttttttactt ccaacaaaat cattcacacg agaaaatctg tctcgtgatc    1440
actttcatgc aaaattaaac taaattttgg tattttttgt caagttcttg ctgttttaag     1500
tcgattattt ggtaatacta tatgtgtgga tatacacatc caagctaatc aataattgat      1560
ctccttctgc ttatcaataa attacaccac attagctaat caagctaata aattacacca    1620
cattctctta tcaatttta tatggtataa ataaaacaac cgactatagg ctacagagtt      1680
ggtattaagg cattattgcc ttctagtcga aggaattttt ttgttatgat aacactcgtg   1740
ggaaaaaaat ccagcctaat atgctcattt aaaggataat tgatttaaat gctttaatca    1800
ttaaaataaa aggttttgc ttttaaaggt taccaccgct taattcatca ttaggagaat      1860
attaactttg atcgaaattc caaaatactt ttttaacaca taagaaaatt ttcagcattt      1920
ttaaataaag ggtacattta ttgggttcaa taaatatgtt tccacgtaaa gtttggaggt   1980
ttaaccacat gaatgttttt tgatttaaaa aacacataaa ttttctagta attacacatt     2040
tttaaccgtc catccagatt gtaataagtg acaaatctga aaacattttt tttttcttg         2100 aatcttgttt aaattctctc tgctgcatac ttgcaggcat ttgaccaacg actatacata    2160
ttgaaagcaa aatatccacc agggatgata gggttagatc ccacattcaa tatcttttgt    2220
ctttgttatt tatgaaaaac aaatatttat caggaaaaaa acgtttcttc tctagtggta    2280
taagtataag ataataacaa aatttaatac ttagttaatg tatttactat cttcaaactt    2340
accatccttc aacattaata ttgatcaatt tttattttt ttactaaact acttccacta        2400
aaaaaatgca aagaagaga tatatattta agtcaaagta attaaagatg gatgggtgat     2460
tcttcagcaa aacggcgccg tagaggtgtc ttatcctaca ttacagctgg gttgtggcag    2520
acatcatagg gcctacgtat atttgagctt tactgtacgt aaagctttaa catatctagt     2580
tagttctcac tgtacaaaca aaacaaaatc caattcgtaa catatataca aatactacta   2640
gtactagatt acgctacgta tacatcgctt tttcgcaaat ttctaaacta atctatacaa   2700
caaacttgaa tgtttgtttt gtaatttatc ttaaaccaaa gttttgaatt gtgcattggg    2760
agctacactc tagtcccctt tttttcccaa aataatctcc ttcatcgac cggttaaagt        2820 atttaaacca acaaatttta atttgttgct gaaggtacaa acatgtcaca tatatagaga   2880
```

-continued

| | |
|---|---|
| cagcatcgtt tatacaaata atgttcgatg ttattggaaa tcaaatataa atacgaatta | 2940 |
| gcgactcact tggtttaata gtttggaaga taatgaaata aaaaatgaat tcaaaggata | 3000 |
| cagagctata tatgtcgggt catttagagc cgtgaccaaa agtttcgtcg taatttctac | 3060 |
| ggtcggtcat aagaaatttt ggacttttct tcacccttt atgaacttct gtatagtttt | 3120 |
| tgtcggatta tatatttgta ttcgtatatt ttttgtttct aataatgata cgtaaattca | 3180 |
| cgataagaaa gacttctttt tatttaattt gatttaaaac ttttgttttt ggaaatgact | 3240 |
| catacacaag gttaaagttt gatggtatcc aatttacaaa aatgtttcga gagtgcgttc | 3300 |
| gagtgtccta ccaccatcgt accaactcgt atgggtttat tattaggttt tttcttcttctt | 3360 |
| tttccaatgt ctttataatt gaaccactct aaatttcttt ttttaaatta ggttaagaat | 3420 |
| cttgaatttt ctgttgattt taaaccaagg ttttcaattc ttcttagcac aaaaaaaaaa | 3480 |
| aaaaggtttt caattattaa agaatctaaa ttttttgagt tcaagagttt aatgatagct | 3540 |
| gaaaagttat gaatgattgc aagtttgcaa cagaatggtc gatgtagtac atatcaaaaa | 3600 |
| catgcatcaa aataaatatt cgtgcttagc aagagaaacg attgaaataa acagaacaat | 3660 |
| cgttaaccac ttaaaaatct tagaataatt ttgtagtgat aattttctgt aagagagagg | 3720 |
| tatcatatct tacaaaaaaa aactcatttc agataaaata atgttgtcca atcgttacca | 3780 |
| agtatgtttt tgctgtcatc agttgtattg taactcgtct cttagccata tagttctaag | 3840 |
| ttttaaatgt tttcaaagac tttacaaaaa taaaataata ataaggtgga atttgtaggg | 3900 |
| ctaaaagcga aaaataaaaa taaaataaaa gtaaagaaac gtctttctca ataagaacac | 3960 |
| agatcccaac ggattcaaac agcaaatttg tgctttgctc ttctctctta ttataatatc | 4020 |
| ctctcaaaaa ccctctccta tatcctccta aagccccccct tccttgtttc tctaccgcaa | 4080 |
| caaagaaaaa acaaaagttt gagaaaaatg gtgtgttcgt tgtgtaacca atgattgggt | 4140 |
| tttagcttac tacttcgaga gattataaga agaaagagt gaagatacat tatagaaaga | 4200 |
| agagaagcag aaaccaaaaa aagaaaacc | 4228 |

<210> SEQ ID NO 4
<211> LENGTH: 1738
<212> TYPE: DNA
<213> ORGANISM: Brassica napus
<220> FEATURE:
<221> NAME/KEY: CDS
<222> LOCATION: (1)..(1647)
<223> OTHER INFORMATION: canola AINTEGUMENTA (ANT) partial cDNA including coding region
<223> OTHER INFORMATION: canola AINTEGUMANTA (ANT)

<400> SEQUENCE: 4

| | |
|---|---|
| atg aag tct ttt tgt gat aat gat gat agt aat acg act aat ttg cta<br>Met Lys Ser Phe Cys Asp Asn Asp Asp Ser Asn Thr Thr Asn Leu Leu<br>1               5                   10                  15 | 48 |
| ggg ttc tcg ttg tct tca aat atg ttg aaa atg ggt ggt gga gaa gct<br>Gly Phe Ser Leu Ser Ser Asn Met Leu Lys Met Gly Gly Gly Glu Ala<br>            20                  25                  30 | 96 |
| ctt tac tca tct tcg tcg tct tca gtt gca act tct tct gtt cca cca<br>Leu Tyr Ser Ser Ser Ser Ser Ser Val Ala Thr Ser Ser Val Pro Pro<br>        35                  40                  45 | 144 |
| cag ctt gtt gtt ggc gac aac agt agc aac tat gga gtt tgc tac ggt<br>Gln Leu Val Val Gly Asp Asn Ser Ser Asn Tyr Gly Val Cys Tyr Gly<br>    50                  55                  60 | 192 |
| tct aac tta gca gct agg gaa atg tat tct caa atg tct gtg atg ccc<br>Ser Asn Leu Ala Ala Arg Glu Met Tyr Ser Gln Met Ser Val Met Pro | 240 |

-continued

```
                65                  70                  75                  80
ctc aga tct gac ggt tct ctt tgc tta atg gaa gct ctc aac aga tct     288
Leu Arg Ser Asp Gly Ser Leu Cys Leu Met Glu Ala Leu Asn Arg Ser
                    85                  90                  95 tct cac tcg aat aat cat cac cat agt caa gtt tca tct cca aag atg     336
Ser His Ser Asn Asn His His His Ser Gln Val Ser Ser Pro Lys Met
                100                 105                 110 gaa gat ttc ttt ggg acc cat cat cac aac aca agt cac aaa gaa gcc     384
Glu Asp Phe Phe Gly Thr His His His Asn Thr Ser His Lys Glu Ala
            115                 120                 125 atg gat ctt agc tta gat agt tta ttc tac aat acc act cat gcg cca     432
Met Asp Leu Ser Leu Asp Ser Leu Phe Tyr Asn Thr Thr His Ala Pro
        130                 135                 140 aac aac aac acc aac ttt caa gag ttc ttt agc ttc cct caa act aga     480
Asn Asn Asn Thr Asn Phe Gln Glu Phe Phe Ser Phe Pro Gln Thr Arg
145                 150                 155                 160 aac cac cat gag gaa gaa aca aga aac tac gag aat gac cct ggt ttg     528
Asn His His Glu Glu Glu Thr Arg Asn Tyr Glu Asn Asp Pro Gly Leu
                165                 170                 175 aca cat gga gga ggg tct ttt aat gta ggg gta tat ggg gaa ttt caa     576
Thr His Gly Gly Gly Ser Phe Asn Val Gly Val Tyr Gly Glu Phe Gln
            180                 185                 190 cag tca ctg agc ttg tcc atg agc cct ggg tca caa tct agc tgc atc     624
Gln Ser Leu Ser Leu Ser Met Ser Pro Gly Ser Gln Ser Ser Cys Ile
        195                 200                 205 act gcc tct cat cac cac caa aac caa act caa aac cac cag cag atc     672
Thr Ala Ser His His His Gln Asn Gln Thr Gln Asn His Gln Gln Ile
    210                 215                 220 tct gaa gct ttg gtc gag aca agt gct gga ttt gag aca aca aca atg     720
Ser Glu Ala Leu Val Glu Thr Ser Ala Gly Phe Glu Thr Thr Thr Met
225                 230                 235                 240 gcg gct gct gct gca aag aag aag aga gga caa gaa gtt gtc gtt gga     768
Ala Ala Ala Ala Ala Lys Lys Lys Arg Gly Gln Glu Val Val Val Gly
                245                 250                 255 cag aaa cag att gtt cat aga aaa tct att gat act ttt gga caa cga     816
Gln Lys Gln Ile Val His Arg Lys Ser Ile Asp Thr Phe Gly Gln Arg
            260                 265                 270 act tcg caa tac cga ggc gtt aca aga cat aga tgg act ggt agg tat     864
Thr Ser Gln Tyr Arg Gly Val Thr Arg His Arg Trp Thr Gly Arg Tyr
        275                 280                 285 gaa gct cat cta tgg gac aat agt ttc aag aag gaa ggt cat agc aga     912
Glu Ala His Leu Trp Asp Asn Ser Phe Lys Lys Glu Gly His Ser Arg
    290                 295                 300 aaa gga aga caa gtt tat ctg ggg ggt tat gat atg gag gag aaa gct     960
Lys Gly Arg Gln Val Tyr Leu Gly Gly Tyr Asp Met Glu Glu Lys Ala
305                 310                 315                 320 gct cga gca tat gat ctt gct gca ctc aag tac tgg ggt ccc tct act    1008
Ala Arg Ala Tyr Asp Leu Ala Ala Leu Lys Tyr Trp Gly Pro Ser Thr
                325                 330                 335 cac act aat ttc tct gtg gag aat tat cag aaa gag att gat gac atg    1056
His Thr Asn Phe Ser Val Glu Asn Tyr Gln Lys Glu Ile Asp Asp Met
            340                 345                 350 aag aac atg act cga caa gaa tat gtt gct cac ttg aga aga aaa acc    1104
Lys Asn Met Thr Arg Gln Glu Tyr Val Ala His Leu Arg Arg Lys Thr
        355                 360                 365 agt ggt ttc tct agg ggt gct tcc atc tat aga gga gtc acc aga cat    1152
Ser Gly Phe Ser Arg Gly Ala Ser Ile Tyr Arg Gly Val Thr Arg His
    370                 375                 380 cac cag cat gga agg tgg caa gct cgg atc ggt aga gtc gct gga aac    1200
```

-continued

```
His Gln His Gly Arg Trp Gln Ala Arg Ile Gly Arg Val Ala Gly Asn
385                 390                 395                 400 aaa gat ctc tac ctt gga act ttc gga act caa gaa gaa gcg gcg gaa      1248
Lys Asp Leu Tyr Leu Gly Thr Phe Gly Thr Gln Glu Glu Ala Ala Glu
                405                 410                 415 gcc tat gat gta gca gct atc aag ttc cgt ggc aca aac gcg gtg act      1296
Ala Tyr Asp Val Ala Ala Ile Lys Phe Arg Gly Thr Asn Ala Val Thr
            420                 425                 430 aac ttt gac ata aca agg tac gat gtt gat cgc ata atg gct agt aac      1344
Asn Phe Asp Ile Thr Arg Tyr Asp Val Asp Arg Ile Met Ala Ser Asn
        435                 440                 445 act ctc ttg tct gga gag atg gct cga agg aac agc aac agc atc gtg      1392
Thr Leu Leu Ser Gly Glu Met Ala Arg Arg Asn Ser Asn Ser Ile Val
    450                 455                 460 gtc cgc aac att agc gac gag gaa gcc gct tta acc gct gtc gtg aac      1440
Val Arg Asn Ile Ser Asp Glu Glu Ala Ala Leu Thr Ala Val Val Asn
465                 470                 475                 480 ggt ggt tcc aat aag gaa gtg ggt agc ccg gag agg gtt ttg agt ttt      1488
Gly Gly Ser Asn Lys Glu Val Gly Ser Pro Glu Arg Val Leu Ser Phe
                485                 490                 495 ccg acg ata ttt gcg ttg cct caa gtt ggt ccg aag atg ttc gga gca      1536
Pro Thr Ile Phe Ala Leu Pro Gln Val Gly Pro Lys Met Phe Gly Ala
            500                 505                 510 aat gtg gtc gga aat atg agt tct tgg act acg aac cct aat gct gat      1584
Asn Val Val Gly Asn Met Ser Ser Trp Thr Thr Asn Pro Asn Ala Asp
        515                 520                 525 ctc aag acc gtt tct ctt act ctg ccg cag atg ccg gtt ttc gct gcg      1632
Leu Lys Thr Val Ser Leu Thr Leu Pro Gln Met Pro Val Phe Ala Ala
    530                 535                 540 tgg gct gat tct taa ttcaatctaa tggctaactc tggttttctt ggtttagggt      1687
Trp Ala Asp Ser
545 ccaagtgttt aagtttatct ccgggtttat ccgtttgaa ctacaattcg g              1738
```

<210> SEQ ID NO 5
<211> LENGTH: 548
<212> TYPE: PRT
<213> ORGANISM: Brassica napus
<220> FEATURE:
<223> OTHER INFORMATION: canola AINTEGUMENTA (ANT)

<400> SEQUENCE: 5

```
Met Lys Ser Phe Cys Asp Asn Asp Asp Ser Asn Thr Thr Asn Leu Leu
1               5                   10                  15

Gly Phe Ser Leu Ser Ser Asn Met Leu Lys Met Gly Gly Gly Glu Ala
                20                  25                  30

Leu Tyr Ser Ser Ser Ser Ser Val Ala Thr Ser Ser Val Pro Pro
            35                  40                  45

Gln Leu Val Val Gly Asp Asn Ser Ser Asn Tyr Gly Val Cys Tyr Gly
        50                  55                  60

Ser Asn Leu Ala Ala Arg Glu Met Tyr Ser Gln Met Ser Val Met Pro
65                  70                  75                  80

Leu Arg Ser Asp Gly Ser Leu Cys Leu Met Glu Ala Leu Asn Arg Ser
                85                  90                  95

Ser His Ser Asn Asn His His Ser Gln Val Ser Ser Pro Lys Met
            100                 105                 110

Glu Asp Phe Phe Gly Thr His His Asn Thr Ser His Lys Glu Ala
        115                 120                 125
```

```
Met Asp Leu Ser Leu Asp Ser Leu Phe Tyr Asn Thr His Ala Pro
130                 135                 140

Asn Asn Asn Thr Asn Phe Gln Glu Phe Phe Ser Phe Pro Gln Thr Arg
145                 150                 155                 160

Asn His His Glu Glu Thr Arg Asn Tyr Glu Asn Asp Pro Gly Leu
            165                 170                 175

Thr His Gly Gly Gly Ser Phe Asn Val Gly Val Tyr Gly Glu Phe Gln
                180                 185                 190

Gln Ser Leu Ser Leu Ser Met Ser Pro Gly Ser Gln Ser Ser Cys Ile
        195                 200                 205

Thr Ala Ser His His His Gln Asn Gln Thr Gln Asn His Gln Gln Ile
210                 215                 220

Ser Glu Ala Leu Val Glu Thr Ser Ala Gly Phe Glu Thr Thr Thr Met
225                 230                 235                 240

Ala Ala Ala Ala Ala Lys Lys Lys Arg Gly Gln Glu Val Val Val Gly
                245                 250                 255

Gln Lys Gln Ile Val His Arg Lys Ser Ile Asp Thr Phe Gly Gln Arg
            260                 265                 270

Thr Ser Gln Tyr Arg Gly Val Thr Arg His Arg Trp Thr Gly Arg Tyr
        275                 280                 285

Glu Ala His Leu Trp Asp Asn Ser Phe Lys Lys Glu Gly His Ser Arg
290                 295                 300

Lys Gly Arg Gln Val Tyr Leu Gly Gly Tyr Asp Met Glu Glu Lys Ala
305                 310                 315                 320

Ala Arg Ala Tyr Asp Leu Ala Ala Leu Lys Tyr Trp Gly Pro Ser Thr
                325                 330                 335

His Thr Asn Phe Ser Val Glu Asn Tyr Gln Lys Glu Ile Asp Asp Met
            340                 345                 350

Lys Asn Met Thr Arg Gln Glu Tyr Val Ala His Leu Arg Arg Lys Thr
        355                 360                 365

Ser Gly Phe Ser Arg Gly Ala Ser Ile Tyr Arg Gly Val Thr Arg His
370                 375                 380

His Gln His Gly Arg Trp Gln Ala Arg Ile Gly Arg Val Ala Gly Asn
385                 390                 395                 400

Lys Asp Leu Tyr Leu Gly Thr Phe Gly Thr Gln Glu Glu Ala Ala Glu
                405                 410                 415

Ala Tyr Asp Val Ala Ala Ile Lys Phe Arg Gly Thr Asn Ala Val Thr
            420                 425                 430

Asn Phe Asp Ile Thr Arg Tyr Asp Val Asp Arg Ile Met Ala Ser Asn
        435                 440                 445

Thr Leu Leu Ser Gly Glu Met Ala Arg Arg Asn Ser Asn Ser Ile Val
450                 455                 460

Val Arg Asn Ile Ser Asp Glu Glu Ala Ala Leu Thr Ala Val Val Asn
465                 470                 475                 480

Gly Gly Ser Asn Lys Glu Val Gly Ser Pro Glu Arg Val Leu Ser Phe
                485                 490                 495

Pro Thr Ile Phe Ala Leu Pro Gln Val Gly Pro Lys Met Phe Gly Ala
            500                 505                 510

Asn Val Val Gly Asn Met Ser Ser Trp Thr Thr Asn Pro Asn Ala Asp
        515                 520                 525

Leu Lys Thr Val Ser Leu Thr Leu Pro Gln Met Pro Val Phe Ala Ala
530                 535                 540

Trp Ala Asp Ser
```

-continued

```
545

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:
      consensus ANT polynucleotide sequence-1

<400> SEQUENCE: 6
atgaagtctt tttgtgataa tgatgatagt aat                              33

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:
      consensus ANT polynucleotide sequence-2

<400> SEQUENCE: 7
acgactaatt tgttagggtt ctcattgtct tcaaatatg                        39

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:
      consensus ANT polynucleotide sequence-3

<400> SEQUENCE: 8
agaatcagcc caagcagcga aaaccggcat ctgcggca                         38
```